United States Patent [19]

Davis

[11] Patent Number: 5,785,641
[45] Date of Patent: Jul. 28, 1998

[54] MALE INDWELLING URETHRAL CATHETER SIZING SYSTEM AND INSERTION METHOD

[75] Inventor: Richard C. Davis, Tampa, Fla.

[73] Assignee: Urocath Corporation, Tampa, Fla.

[21] Appl. No.: 646,925

[22] Filed: May 8, 1996

[51] Int. Cl.⁶ ............................................. A61F 2/02
[52] U.S. Cl. ................................. 600/30; 604/101
[58] Field of Search .................... 604/96, 101, 104, 604/264, 275, 280; 600/29–31; 128/DIG. 25

[56] References Cited

U.S. PATENT DOCUMENTS

| | | | |
|---|---|---|---|
| 4,350,161 | 9/1982 | Davis, Jr. | |
| 4,932,938 | 6/1990 | Goldberg et al. | 604/96 |
| 4,932,956 | 6/1990 | Reddy et al. | 604/101 |
| 4,946,449 | 8/1990 | Davis, Jr. | 604/256 |
| 5,002,558 | 3/1991 | Klein et al. | 604/101 |
| 5,007,898 | 4/1991 | Rosenbluth et al. | 604/101 |
| 5,041,092 | 8/1991 | Barwick | 604/104 |
| 5,496,271 | 3/1996 | Burton et al. | 604/101 |

*Primary Examiner*—Mark Bockelman
*Attorney, Agent, or Firm*—Griffin, Butler Whisenhunt & Szipl

[57] ABSTRACT

An indwelling urethral catheter sizing system comprises sets of substantially equal length indwelling urethral catheters (14) having various balloon spacings (a, b, c), from bladder balloons (2) to urethral anchoring cuff balloons (36). A method of implanting an indwelling urethral catheter from the sets involves first determining a patient's interballoon urethral segment length, from his bladder to his bulbous urethra immediately downstream of what remains of his prostate gland. A urethral sizing catheter having a balloon spacing corresponding to the interballoon urethral segment length is inserted in the patient to determine the clinical length of the patient's urethral tract from his bladder to his penile meatus. A male indwelling urethral catheter is then chosen from the sets having a balloon spacing corresponding to the patient's interballoon urethral segment length and the clinical length determined with the urethral sizing catheter. The urethral sizing catheter can be used for filling and voiding the bladder.

13 Claims, 3 Drawing Sheets

MALE INDWELLING URETHRAL CATHETER SIZING SYSTEM AND INSERTION METHOD

BACKGROUND OF THE INVENTION

This invention relates to urethral catheters and more specifically to a male indwelling urethral catheter which, after it is inserted and anchored into position, does not extend beyond a patient's penile meatus and allows the patient to urinate in a substantially normal manner.

Indwelling urethral catheters of the type to which this invention relates were first disclosed in U.S. Pat. No. 4,350,161 to Richard C. Davis, Jr. A common feature of such catheters is a valve which, when the catheter is properly anchored in the patient's urethra, is positioned in the patient's penile urethra and can be activated by application of a force external to the penis. A further feature of such a catheter is that it is dimensioned and installed so that its downstream tip does not extend beyond the penis meatus in any patient position. As is set forth in U.S. Pat. No. 4,350,161 of Richard C. Davis, Jr. a method of inserting such an indwelling urethral catheter includes the step of determining the length of the patient's urethral tract from his bladder to his penile meatus. Thus, since the advent of the indwelling urethral catheter of the type described above, proper sizing of the catheter has always been appreciated as a critical element in a protocol for positioning the device and in its proper function.

During development of this catheter it has come to be better appreciated that as a body moves, a bladder and urethra shift and stretch relative to one another. It has been determined that overall urethral length is generally shortest when a patient is lying down and lengthens when the patient is sitting or standing. Thus, it has been determined that a properly sized male indwelling urethral catheter of this type must be short enough to remain totally inside the patient's urethra in all positions, but yet long enough to allow easy access to the valve located in the patients penile urethra for voiding and for removal of the catheter itself.

If it is sized too long, the catheter may occasionally protrude from the tip of the penis, potentially causing pain, swelling, and infection. If the catheter is too short, the patient may not be able to easily access the valve to properly actuate it. Further, the patient may have difficulty removing the catheter.

Another feature of the indwelling urethral catheter described in U.S. Pat. No. 4,350,161 to Richard C. Davis, Jr. is that it includes not only a bladder balloon but also an anchoring urethral cuff balloon along a catheter drainage shaft for inflating in the patient's urethra. A primary purpose of the urethral anchoring cuff balloon, as was described in U.S. Pat. No. 4,350,161, is to prevent retrograde movement of the catheter into the bladder by using the prostatic urethra as a buttress against which the urethral anchoring cuff balloon is juxtaposed.

To meet different lengths of normal adult urethral tracts, indwelling urethral catheters of the type of this invention, have been, to date, manufactured in six different lengths so that most any length of an adult male penis and urethral tract can be accommodated. However, notwithstanding this, sizing problems continue to be encountered. In this regard, until recently, an indwelling urethral catheter of the type of this invention was fitted to a patient by first placing a measuring catheter, having a bladder balloon and drainage shaft extending beyond the patient's penile meatus, in the patient. By noting the position of the penile meatus along the measuring catheter's drainage shaft, with the patient in various positions, the overall length of the patient's urethral tract was determined. An indwelling urethral catheter was then chosen from the six different lengths corresponding to the overall length of the patient's urethral tract. Using this method, however, problems have continually been encountered in choosing the proper length catheters. That is, after catheters, whose lengths were determined as described above, have been installed it has been found that they often have not remained in their preferred positions. In some cases they have shifted downstream to extend beyond a patient's penile meatus when the patient was in a lying position and in other cases they have shifted upstream so far from the meatus that the patient has not been able to activate the valve to urinate. Because of this, it has sometimes been necessary to try various size catheters in a patient, one after the other—even though the patient was previously measured—until a catheter of the correct size, if ever, was found. Thus, in many cases, catheter sizes have actually been determined as much by trial and error as by measuring, if at all. Such trial and error has resulted in discomfort for patients and has proven to be expensive, since it has resulted in the expenditure of many catheters and much time and effort; and often patients were not able to be fitted at all.

The problem has been that some inserted indwelling urethral catheters, of the type of this invention, have experienced undue linear movement along urethral tracts. That is, sometimes they have appeared to be in their correct positions but then at other times they have moved linerally, within the urethral tract, to inappropriate positions. Thus, when some catheters were initially sized using the above-described method, which relied solely on the bladder-to-meatus length, they were occasionally noted to shift downstream in the urethra; thereby appearing to be "too long", and their tips intermittently protruded from the penile meatus. It has been assumed that such shifting represented "device failure"; presumably the bladder balloon had leaked thus allowing downstream migration. An opposite situation has been noted in some patients who at first could easily access their valves but who, over time, had increasing difficulty accessing their valves because their catheters migrated upstream. Again, this was previously interpreted as a "device failure" whereby the urethral anchoring cuff balloon was thought to have deflated allowing such upstream migration.

Therefore, it is an object of this invention to provide a system of urethral sizing, or measuring, catheters and a method sf its use, which allows accurate measuring of the length of a patient's urethral tract so that an appropriate-length indwelling urethral catheter can be chosen which fits the patient's urethral tract.

Similarly, it is an object of this invention to provide a method for measuring a patient's urethral tract for determining an appropriate clinical length of a indwelling urethral catheter which is accurate, uncomplicated, fast, and not unduly expensive. It is also an object of this invention to provide a system of indwelling urethral catheters which includes sets of urethral catheters of substantially the same lengths but having different features for accommodating patients with different urethral anatomies which vary due to their preexisting clinical conditions.

SUMMARY

According to principles of this invention, it has been determined that a cause of this linear shifting is that an anchoring urethral cuff balloon prefers to reside in the bulbous urethra, regardless of its position. It has been thus determined that not only must the overall urethral length be considered, but the distance between the bladder neck orifice and the bulbous urethra is also critical. This distance is referred to herein as the interballoon urethral segment length or "urethral segment length".

Further according to principles of this invention, an indwelling urethral catheter system and method of its use involves sets of catheters having substantially the same lengths, but having bladder balloons and urethral anchoring cuff balloons spaced differently from one another in order to accommodate various interballoon urethral segment lengths of patients. Both urethral sizing catheters and indwelling urethral catheters include sets of catheters with variously spaced bladder and urethral-anchoring-cuff balloons.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Figure 1:
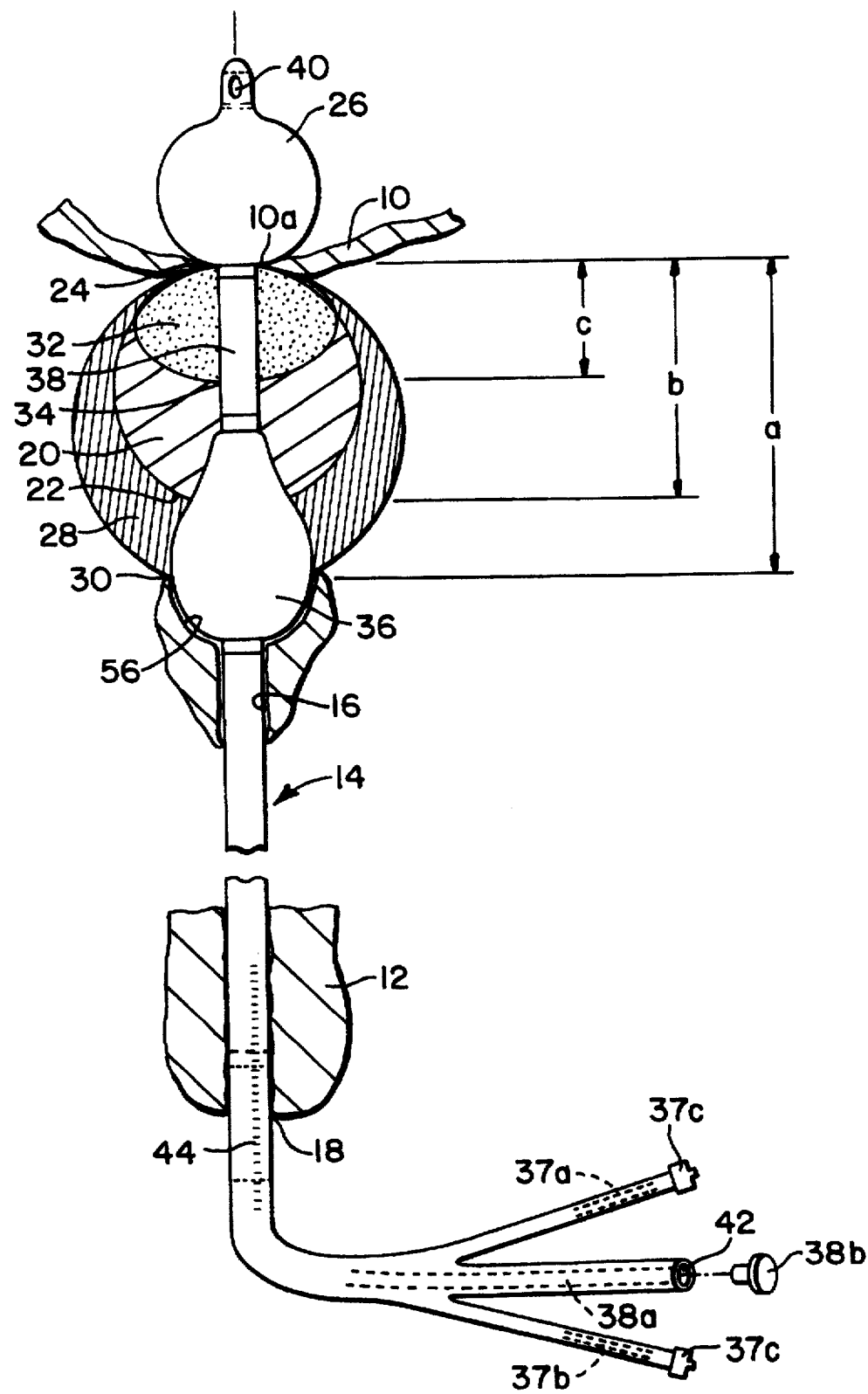
FIG. 1 is a schematic lengthwise, partially crosssectional, partially-exploded, view of a single urethral sizing catheter of a set of urethral sizing catheters of this invention when mounted in a patient, with possible prostate sizes being indicated thereon diagrammatically.

This invention is based on the realization that the distance between the bladder neck orifice and the bulbous urethra, which shall be referenced herein as the "interballoon urethral segment length" and as the "prostatic urethral length", varies tremendously among patients. Such a difference in interballoon urethral segment lengths is illustrated in FIG. 1 where are shown diagrammatically: a patient's bladder 10, the patient's penis 12, and a urethral sizing catheter 14 extending through a urethral tract 16 from the bladder 10 to beyond a penile meatus 18. For purposes of illustration, three different size interballoon urethral segment lengths (i.e. prostate gland or prostate Fossa as the case may be) are represented diagrammatically on FIG. 1. It should be understood that individual patients will have only one of these interballoon urethral segment lengths; however, all three are depicted on FIG. 1 so that a reader can compare the different size interballoon urethral segment lengths with the interballoon spacing (balloon spacing) of a most-often-used (or normal size) sizing catheter and the corresponding indwelling urethral catheter.

A normal-size prostate gland 20 has a downstream side 22 which is located approximately four centimeters from the interior surface of a bladder neck orifice 10a (or downstream side 24 of a bladder balloon 26). This four centimeter spacing is represented by the letter "b" in FIG. 1. However, an enlarged, or hypertrophic prostate gland 28 has a downstream side 30 (as used herein, "downstream" means away from the bladder 10 toward the meatus 18 and "upstream" means toward the bladder 10 and away from the meatus 18) which is spaced approximately 5.5 cm from the downstream side 24 of the bladder balloon 26 in the bladder 10. This 5.5 cm measurement is signified by the letter "a" in FIG. 1. Finally, a post prostatectomy prostatic Fossa 32, which is essentially what is left when a prostate is removed (or at least diminished), has a downstream side 34 which is spaced approximately 2.0 cm from the downstream side 24 of the bladder balloon 26 when it is in the bladder 10. This downstream side of the bladder balloon 26 can also be influenced to some extent by the position of the bulbous, urethra 56. In this regard, when a patient's prostate is removed, it sometimes happens that some of the bladder must also be removed and reconstructed. In this process, these elements move relative to one another to some extent.

In any event, this 2.0 cm measurement is indicated by the letter "c" in FIG. 1. It should be understood that these measurements are only given as approximations and that they can vary significantly from patient to patient. However, it can be seen from these approximations, in FIG. 1, that the relative interballoon urethral segment lengths ("b", "a", & "c") of patients—and thus necessary catheter balloon spacings—can vary by a factor of nearly three (comparing "a" with "c").

The urethral sizing catheter 14 is shown as having a urethral anchoring cuff balloon 36 which is spaced along a shaft 38 of the catheter 14 from the downstream side 24 of the bladder balloon 26 thus defining a catheter interballoon distance. Thus, the overall upstream structure of the bladder balloon 26 and the urethral anchoring cuff balloon 36 for this sizing catheter 14 is quite similar to that of an indwelling urethral catheter of the type with which this invention relates.

The bladder balloon 26 and the urethral anchoring cuff balloon 36, shown in FIG. 1, are spaced from one another a correct amount to appropriately anchor the urethral sizing catheter 14 on the normal-size prostate gland 20, which it inflatingly engages. That is, when the bladder balloon 26 and the urethral anchoring cuff balloon are inflated, as shown, they apply pressure to opposite sides of the normal-size prostate gland 20 for holding the urethral sizing catheter 14 against retrograde movement (up into the bladder 10) and against downstream movement (out of the penile meatus 18).

According to this invention, if the patient had an enlarged prostate gland 28, or a missing prostate gland 32 as a result of having prostatectomy surgery, a different respective urethral sizing catheter 14 would be selected, one with its catheter interballoon distance being appropriate so that the balloons impinge on opposite sides of the prostate gland, or prostate fossa as the case may be, on which the urethral sizing catheter is to be mounted. In all cases, however, the urethral anchoring cuff balloon resides in the bulbous urethra. In the past, all sizing catheters have had essentially the same balloon configuration. Further, all indwelling urethral catheters have had essentially the same interballoon distance configuration. The urethral sizing catheter 14, in addition to having two inflation lumens 37a, 37b—for inflating the bladder balloon 26 and the urethral anchoring cuff balloon 36 through Robert's valves 37c (see U.S. Pat. No. 5,041,092 to Barwick as well as the previously-described U.S. Pat. No. 4,350,161 to Davis for such disclosures)—has a drainage/filling lumen 38a which connects bladder openings 40 with an exterior opening 42 (these elements being shown schematically). Using this drainage/filling lumen 38a of the urethral sizing catheter 14, the bladder 10 can be filled and voided.

Further, the urethral sizing catheter 14 has graduation indicia 44 along its length so that one can "read" the position of the penile meatus 18 along the catheter shaft 38 for determining the appropriate overall clinical length of an indwelling urethral catheter while the patient moves throughout a series of positions and ranges of motion.

Figure 2A:
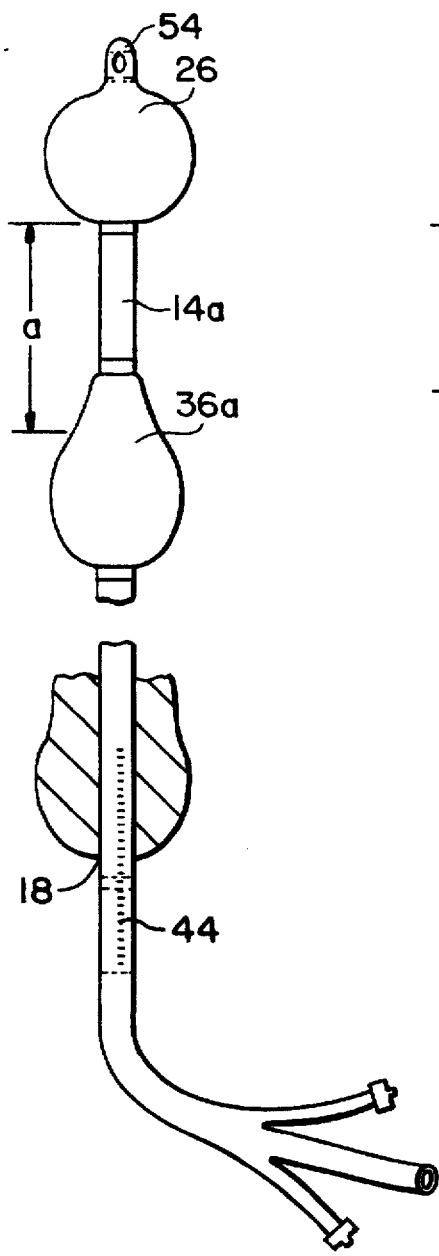
FIGS. 2A–2C are truncated schematic lengthwise cross-sectional views depicting urethral sizing catheters of a urethral sizing catheter set of this invention with a penis being shown schematically on each of them in cross-section; and, FIGS. 3A–3C are schematic lengthwise cross-sectional views depicting indwelling urethral catheters of a set of this invention with a penis being shown schematically on each of them in cross-section.
Figure 2B:
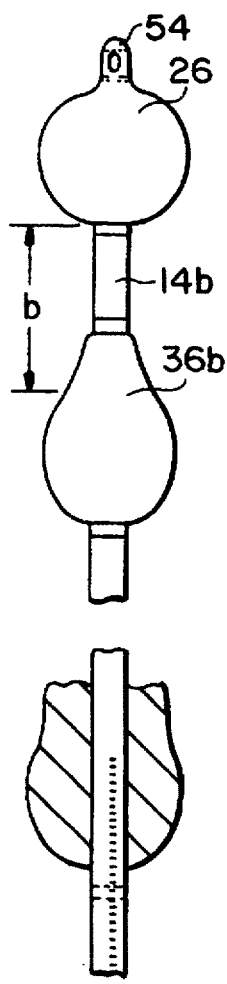
Figure 2C:
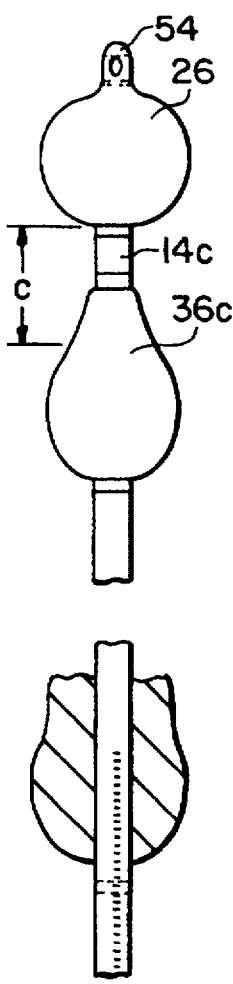

FIGS. 2A–2C depict a set of urethral sizing catheters 14a–14c. As can be seen in FIGS. 2A–2C each urethral sizing catheter of this set has a different interballoon spacing (interballoon) between the bladder balloon 26 and the respective urethral anchoring cuff balloon 36a–c corresponding to a different interballoon urethral segment length "a", "b", "c", thus defining 3 different interballoon spacings.

Figure 3A:
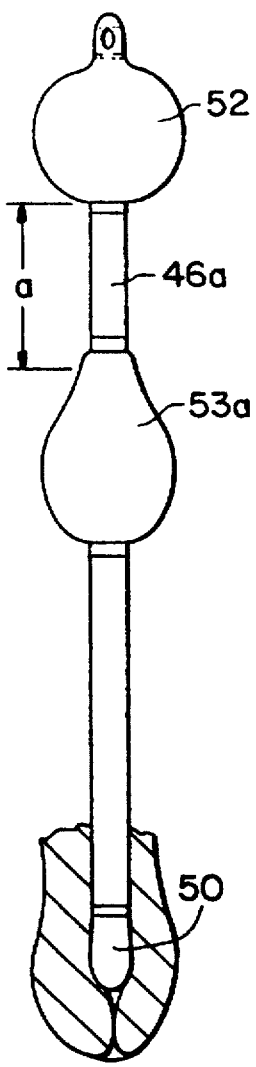
Figure 3B:
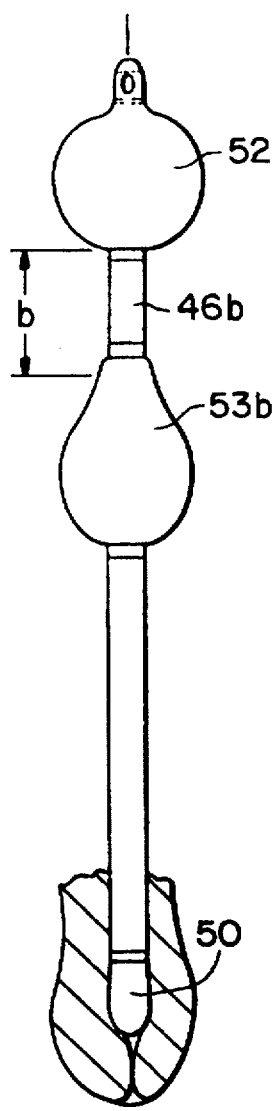
Figure 3C:
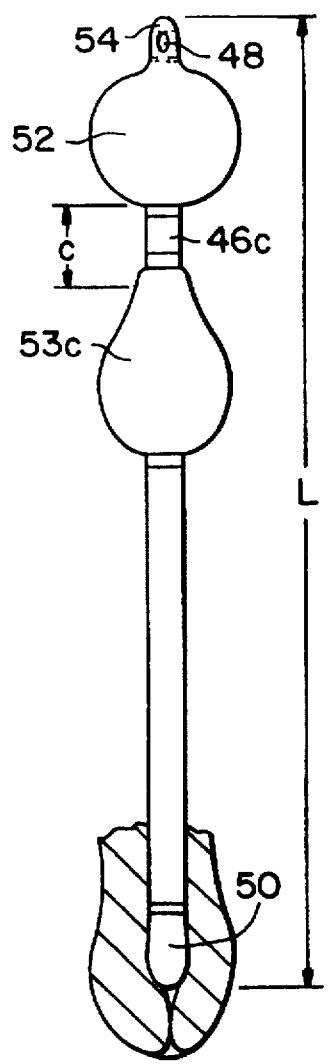

FIGS. 3A–C depict respectively three different indwelling urethral catheters 46a, 46b, 46c of a urethral catheter set. Each of the catheters 46a–46c of the indwelling urethral catheter set generally has a drainage lumen communicating with bladder openings 48 in a Murphy tip 54, a valve 50 for controlling flow through the drainage lumen, and two inflation lumens (not shown) for inflating the bladder balloon 52 and the urethral anchoring cuff balloon 53a–c. The details of this catheter are not described herein inasmuch as the details do not relate to this invention. However, details of such male indwelling urethral catheters can be found in U.S. Pat. Nos. 4,350,161; 5,041,092; and, 4,932,938.

In any event, it can be seen that each of the indwelling urethral catheters of the set depicted in FIGS. 3A–C has approximately the same overall urethral length L. However, the respective spacings between the bladder balloons 52 and the urethral anchoring cuff balloons 53a–c that is the balloon spacing corresponding to interballoon urethral segment lengths a, b, c are quite different for each member of the set.

Describing now a method of fitting an indwelling urethral catheter of the type of this invention to a patient, an investigator first determines a patient's interballoon urethral segment length. The investigator does this by examining the patient's medical history to determine if the patient's prostate gland has not been removed. If the prostate gland has not been removed, the investigator determines the size of the patient's prostate gland indirectly by rectal exam or directly by measuring the length of the prostatic urethra using cystoscopic or ultrasonic methods. By doing this the investigator can then determine which of the urethral sizing catheters 36a–c depicted respectively in FIGS. 2A–2C (the one with a balloon spacing corresponding to the interballoon urethral segment length of the patient) should be used. The investigator then:

1. With the patient recumbent, washes the patient's penis and swabs it with a Betadine solution using standard sterile techniques and prepping procedures.

2. Applies an anesthetic lubricant to the urethral sizing catheter 36a, 36b or 36c which has been chosen and inserts the catheter, Murphy tip 54 first, into the patient's bladder through the patient's urethral meatus 18. The bladder balloon 26 is inflated with a volume of sterile saline solution through an inflation valve (not shown) and an inflation lumen (not shown) and a gentle external axial traction is applied to the catheter to snug the bladder balloon 26 against a base of the bladder neck orifice 10a.

3. While applying continual axial traction, a volume of sterile saline is instilled through the inflation (Roberts) valve, thus inflating the urethral anchoring cuff balloon 36a, 36b, or 36c in the patient's bulbus urethra 56 (FIG. 1) to the point of mild discomfort for the patient. (Note that the bulbous urethra is always the preferred anchoring position of the anchoring cuff balloon 36a–c within the urethra).

4. The bladder 10 is then slowly instilled with a volume of sterile saline through the drainage/filling lumen 38a of the urethral sizing catheter 14a, 14b or 14c. The drainage lumen is then occluded with a plug 38b (shown schematically) and the patient is observed from a few minutes up to as long as several days. In some cases it is necessary to fill and void bladders a number of times in order to condition patients who have not had full bladders for a long time, for example.

5. Once the patient is able to tolerate the urethral sizing catheter with a full bladder, without discomfort, leakage, spasms, or other difficulties, the operator reads and notes the patient's overall clinical urethral length from the graduation indicia 44 on the urethral sizing catheter at the penile meatus 18 when the patient is in prone, sitting, and standing positions, with little or no traction on the catheter. If any difficulties in the patient are noted, adjustment in balloon volumes can be made to "custom-fit" it for a given patent. The volumes used for inflating the balloons for achieving particular graduation-indicia readings are also noted. The urethral sizing catheter is then removed (after voiding the bladder) by deflating the bladder balloon 26 and the urethral anchoring cuff balloon 36a, 36b or 36c and the urethral sizing catheter is withdrawn from the patient's penis by applying gentle axial traction.

6. An indwelling urethral catheter is selected 46a, 46b or 46c having a balloon spacing between its bladder balloon 52 and its urethral anchoring cuff balloon 53a, b, or c which corresponds to the interballoon urethral segment length "a", "b" or "c" as determined above. As stated above, the interballoon urethral segment length "a" normally corresponds to a patient with an enlarged prostate gland, the interballoon urethral segment length "b" normally corresponds to a patient with a normal size prostate gland, and the interballoon urethral segment length "c" normally corresponds to a patient who has had his prostate removed. However, there also exists variations, modifications, and exceptions to these 3 general categories. The catheter chosen also has a length which corresponds to the graduation-indicia reading taken on the urethral sizing catheter. That is, the catheter chosen when inserted and anchored in the patient, would not quite extend along the urethra to the graduation-indicia reading, in all positions of the patient, but yet its downstream tip (and its evacuation valve) are relatively close to the penile meatus in all positions of the patient.

7. The indwelling urethral catheter which has been selected is then inserted and its bladder balloon 52 and urethral anchoring cuff balloon 53a, b or c are inflated sequentially in that order, with the identical volumes as were determined by the sizing catheter.

Sizing is usually required only once and this procedure accurately and efficiently accomplishes a correct sizing of an indwelling urethral catheter on an initial insertion nearly every time. The entire procedure requires less than five minutes, is only slightly uncomfortable, and should not be painful for patients.

Further, any "mis-sizing" of the indwelling urethral catheter will usually be noted immediately after the indwelling urethral catheter has been placed and is certain to be observed within minutes (not days) once the patient is observed to void and to ambulate around the office.

In the past, it has only been necessary to have one type of urethral sizing catheter and six different lengths of indwelling urethral catheters. However, with this new system, it is anticipated that there will be at least three different sizes of urethral catheters, each having approximately the same length but each having different balloon spacings to accommodate the different interballoon urethral segment lengths. Further, it is anticipated that there will now be up to 18 different indwelling urethral catheter sizes. That is, there will still be up to six different overall clinical catheter lengths, but for each length there will be a set of at least three different balloon spacings to accommodate various interballoon urethral segment lengths of patients.

It will be appreciated by those of ordinary skill in the art that the method of determining the proper size indwelling urethral catheter, and the unique indwelling urethral catheter sets themselves, of this invention significantly reduce the chance of linear shifting within a urethra, thus improving the operation of male indwelling urethral catheters as well as reducing the time required for sizing them and decreasing discomfort to patients using them. Further, by improving the accuracy of initial sizing, expenses are reduced.

An important aspect of this invention is that both overall urethral length and the interballoon urethral segment length must be taken into consideration. Also, changes caused by filling a bladder are also taken into consideration.

It should be appreciated by those of ordinary skill in the art that the step of instilling the bladder with a volume of sterile saline through the drainage/filling lumen 38 of the urethral sizing catheter 14, and then occluding the drainage lumen with a plug 38b before the patient is observed and measured, is an important and new step in the sizing method. In this regard, prior art sizing catheters -measured patients without filling their bladders. Many patients, because they are incontinent, were not use to having filled bladders and were unable to tolerate this. Thus, the sizing catheter of this invention provides information to an operator as to the patients level of tolerance. Similarly, the operator can use the sizing catheter for "exercising" a patient's bladder by filling and voiding the bladder to prepare the patient for using an indwelling urethra catheter. Also, by filling the bladder prior to taken an overall clinical urethral length measurement, a more accurate clinical length is determined. That is, filling a bladder can influence catheter length.

The invention claimed is:

1. A method of determining a clinical length of an indwelling urethral catheter of a type for extending from a male's bladder to close to his penile meatus without extending outside his body, said method comprising the steps of:

determining the male's urethral segment length, from his bladder to a bulbous urethra immediately downstream of what remains of his prostate gland;

choosing an elongated urethral sizing catheter having a bladder expandable retainer at an upstream end thereof and a urethral expandable retainer spaced along the urethral sizing catheter in a downstream direction from the bladder expandable retainer an expandable-retainer spacing which corresponds to the patient's urethral segment length, said urethral sizing catheter having an overall length substantially greater than an overall length of the patient's urethral tract with graduation indicia thereon;

inserting the urethral sizing catheter into the patient's urethral tract and expanding the bladder expandable retainer in the patient's bladder and the urethral (anchoring cuff balloon) expandable retainer in the patient's bulbous urethra so that the urethral sizing catheter extends outside of the patient's penile meatus;

noting the position of the penile meatus on the urethral sizing catheter relative to the graduation indicia and thereby determining a desired length for an indwelling urethral catheter; and, choosing an indwelling urethral catheter having a desired length and having an expandable-retainer spacing corresponding to the urethral segment length of the male and having a clinical length which is less than the length of the male's urinary tract.

2. A method as in claim 1 wherein said said indwelling catheter is chosen from a set of indwelling catheters which includes urethral catheters having approximately a same clinical length but having at least three substantially different expandable-retainer spacings corresponding to a normal prostate gland, an enlarged prostate gland, and a diminished prostate gland.

3. A method as in claim 2 wherein is further included the step of filling said patient's bladder with liquid through a drainage/filling lumen of said urethral sizing catheter before noting the position of the penile meatus on said urethral sizing catheter.

4. A method as in claim 3 wherein the position of said penile meatus along said urethral sizing catheter is noted while the patient is in at least two of the following positions: a prone position, a sitting position, and a standing position.

5. A method as in claim 1 wherein is further included the step of filling said patient's bladder with liquid through a drainage/filling lumen of said urethral sizing catheter before noting the position of the penile meatus on said urethral sizing catheter.

6. A method as in claim 5 wherein the position of said penile meatus along said urethral sizing catheter is noted while the patient is in at least two of the following positions: a prone position, a sitting position, and a standing position.

7. A method as in claim 1 wherein said sizing catheter is chosen from a set of urethral sizing catheters with each of said sizing catheters of the set having a different expandable-retainer spacing than that of other sizing catheters of the set and each of said urethral sizing catheters of the set of urethral sizing catheters having graduated markings along its length.

8. A urethral-catheter system comprising a urethral sizing catheter for measuring a distance from a patient's bulbous urethra to the patient's penile meatus and an indwelling urethral catheter for controlling flow of urine through the patient's urethra with a valve therein, wherein;

the urethral sizing catheter has a shaft formed of non-separable parts which is longer than most patients' urethral tracts, the urethral sizing catheter having a bladder expandable retainer at an upstream end of the shaft, an urethral expandable retainer spaced from the bladder expandable retainer a specified sizing-catheter expandable-retainer spacing, and graduation indicia along the shaft downstream of the expandable retainers;

the indwelling urethral catheter including a valve therein for controlling urine flow through the indwelling urethral catheter, a bladder expandable retainer at an upstream end thereof, and a urethral expandable retainer spaced along the indwelling urethral catheter in a downstream direction from the bladder expandable retainer an indwelling expandable-retainer spacing which approximates that of the sizing-catheter expandable- retainer spacing of the sizing catheter.

9. A urethral-catheter system as in claim 8 wherein said urethral sizing catheter is one of a set of urethral sizing catheters and said indwelling urethral catheter is one of a set of indwelling urethral catheters, each of said sets including at least three respective sizing and indwelling catheters, with each of the at least three respective sizing and indwelling catheters having a different expandable-retainer spacing than other members of the set.

10. A urethral-catheter system as in claim 9 wherein all three of the urethral sizing catheters have graduated markings along the shafts thereof to measure the location of a penile meatus.

11. A urethral-catheter system as in claim 8 wherein each of the urethral sizing catheters has graduated markings along the shafts thereof to measure the location of a penile meatus.

12. A urethral-catheter system as in claim 8 wherein the shaft of each urethral sizing catheter of the set includes a drainage/filling lumen for voiding and filling a bladder and a means for selectively occluding and voiding the drainage/filling lumen.

13. A urethral-catheter system as in claim 12 wherein said means for selectively occluding can be activated for occluding and voiding from a downstream end portion of said shaft.

* * * * *